United States Patent [19]

Bacal et al.

[11] 4,257,409
[45] Mar. 24, 1981

[54] DEVICE FOR TREATMENT OF SPINAL CURVATURE

[76] Inventors: Kazimierz Bacal, ul. Akademicka 8, Zielona Góra; Lech Wierusz, Pl. Browarniany 2, Świebodzin, both of Poland

[21] Appl. No.: 28,424

[22] Filed: Apr. 9, 1979

[30] Foreign Application Priority Data

Apr. 14, 1978 [PL] Poland ............................ 206130

[51] Int. Cl.³ .............................................. A61F 5/00
[52] U.S. Cl. .................................. 128/69; 128/92 R; 411/437
[58] Field of Search .................. 128/68, 69, 75, 78, 128/92 R, 92 A, 92 E, 92 ED, 92 EA; 85/32 V, 38

[56] References Cited

U.S. PATENT DOCUMENTS

| | | | |
|---|---|---|---|
| 657,256 | 9/1900 | Tipton | 85/38 |
| 752,074 | 2/1904 | Jackson | 85/32 V |
| 795,242 | 7/1905 | Weiss | 85/38 |
| 1,638,165 | 8/1927 | Rau | 85/38 |
| 3,878,757 | 4/1975 | Puklus, Jr. | 85/32 V |

FOREIGN PATENT DOCUMENTS

| | | |
|---|---|---|
| 2424458 | 12/1974 | Fed. Rep. of Germany . |
| 2275679 | 1/1976 | France . |
| 2244446 | 3/1977 | France ............... 128/69 |
| 7403650 | 9/1975 | Netherlands ......... 85/32 V |
| 453654 | 6/1968 | Switzerland ......... 85/32 V |

OTHER PUBLICATIONS

Cotrel, Techniques Nouvelles dans le Traitement de la Scoliose Idiopatique; Internat'l. Ortho. SICOT, vol. 1, No. 4, 1978, Pub. Springer Internat'l.

*Primary Examiner*—Robert W. Michell
*Assistant Examiner*—Arthur S. Rose

[57] ABSTRACT

The subject of the invention is a device for surgical treatment of spinal curvatures, especially of scoliotic and kyphotic curvatures.

The device is provided with hooks varying in design and a distraction spacer, and comprises a longitudinal contractor fixed in holes and a transverse contractor adjusting the position of the spacer in relation to the longitudinal contractor.

The longitudinal contractor is in the form of a profiled bar 1 provided at one end with a bearing surface 2 and at the other end—with a longitudinal cut forming tips 3 and 4 which are plastically deformed after placing and fixing of the bar 1 in hooks. The transverse contractor comprises a threaded pin 9 provided at one end with a fixed catch 10 and at the other end—with a tilting catch 11 with a threaded lock provided at one end with a bevelled internal surface 12 and at the other end—with a recess which has protruding elements 13. The said elements, after plastic deformation, set and block the position of the lock on the pin.

1 Claim, 7 Drawing Figures

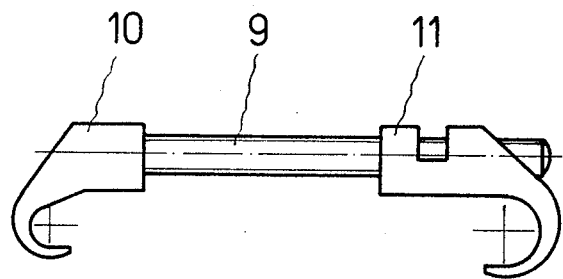
Fig. 3
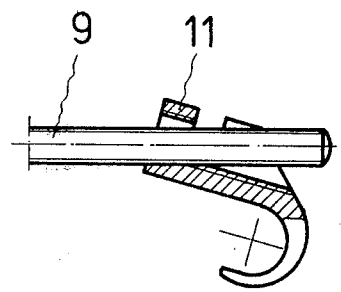
Fig. 4
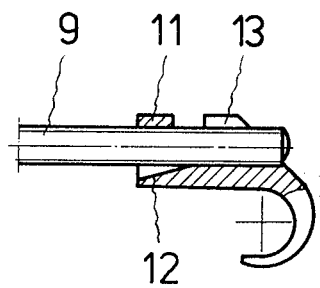 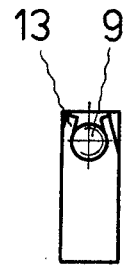
Fig. 5  Fig. 6

DEVICE FOR TREATMENT OF SPINAL CURVATURE

The subject of the invention is a device for surgical treatment of spinal curvatures, especially of scoliotic and kypnotic curvatures.

Devices used in surgical treatment of spinal curvatures are usually designed for distraction of the affected section of the spine and simultaneous replacement of the removed section — for a determined period of time — by a spacer placed from the concave side of the curvature, and/or contracting of the curved section of the spine by means of a flexible element fixed from the convex side of the curvature.

From the Polish Pat. No. 96,695 there is known a distractor used for stretching of the spine and designed in the form of a profiled spacer mounted in hooks fixed between appropriate vertebrae of a curved spine.

Contractors designed for contracting of curved sections of the spine are in the form of springs known from the practice and provided with with hooks or threaded pins on which the hooks are positioned by means of nuts.

There is also known a device, as specified by Y. Contrel, comprising a spacer, a longitudinal contractor in the form of a threaded pin provided with hooks, and two transverse pullers in the form of threaded bars with fixed and slidable hooks. The threaded pin of the longitudinal contractor is provided with slidable hooks. Each hook is provided with a threaded hole for a screw which fixes the hook in an appropriate position on the pin. The transverse pullers also have slidable hooks which are provided with screws for fixing of the hooks in appropriate positions.

The aforesaid devices comprise a large number of threaded bars and screw-type elements for fixing of hooks in appropriate positions, which makes the operation last for a long time. Generally employed practice of cutting off too long pins and screw-type elements may reduce strength and biochemical resistance parameters of implants and cause disadvantageous changes in patient's organism.

The object of the invention is to design a device which eliminates the aforesaid drawbacks. The device is provided with hooks appropriately varying in design and fixed between vertebrae of the spinal sections under treatment, and with a known surgical spacer used for distraction of the spine. The device comprises a longitudinal contractor in the form of a profiled bar, one end of which is provided with a bearing surface, whereas the other end is cut longitudinally, the said bar being positioned in the holes of the previously fixed hooks, one of which is provided with radial bends, and a transverse contractor fixing the aforesaid longitudinal contractor in a previously installed distraction spacer. The transverse contractor is in the form of a threaded pin, one end of which is provided with a fixed catch, whereas the other end is provided with a tilting catch having a thread lock. The thread lock is provided with a threaded hole, one end of which has a bevelled internal surface and the other end has a recess whose diameter is equal to the diameter of the thread. Protruding elements—after bending—protect the pin against tilting and slipping out of the lock.

After fixing of the longitudinal contractor in the holes of the hooks their position is adjusted on the bar by means of plastic deformation of the tips in radial recesses of one of the hooks, then position of the contractor in relation to the distraction spacer is adjusted by means of the tilting catch of the transverse contractor. The device for treatment of spinal curvatures according to the invention is of simple design, is easy in operation for a surgeon, and can be used for treatment of complicated cases of spinal curvatures.

Simple design of components of the device renders it possible—during an operation—to use bars of lengths varying in accordance with requirements, which eliminates the necessity of cutting off the bars after fixing them in the patient's organism.

The subject of the invention is illustrated by means of an example of its realisation in drawings, where.

FIG. 3 shows a side view of the transverse contractor,

FIG. 4 shows a tilted slidable catch of the transverse contractor in a half section, FIG. 5 shows the slidable catch of the transverse contractor, fixed on the pin, FIG. 6 shows a section of the transverse slidable catch.

Figure 1:
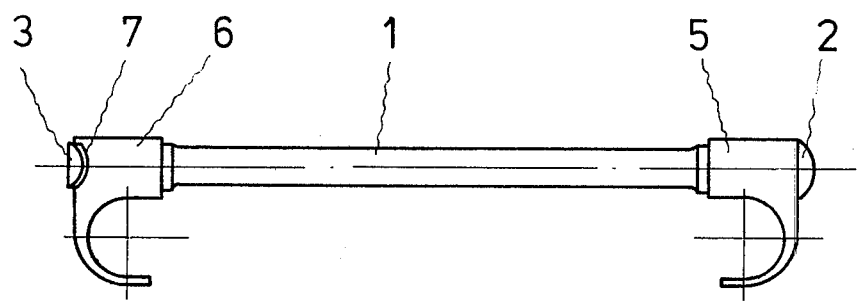
FIG. 1 shows a side view of the longitudinal contractor.
Figure 2:
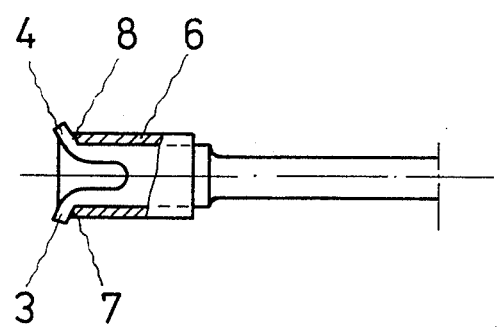
FIG. 2 shows a top view of the tip of the longitudinal contractor.
Figure 7:
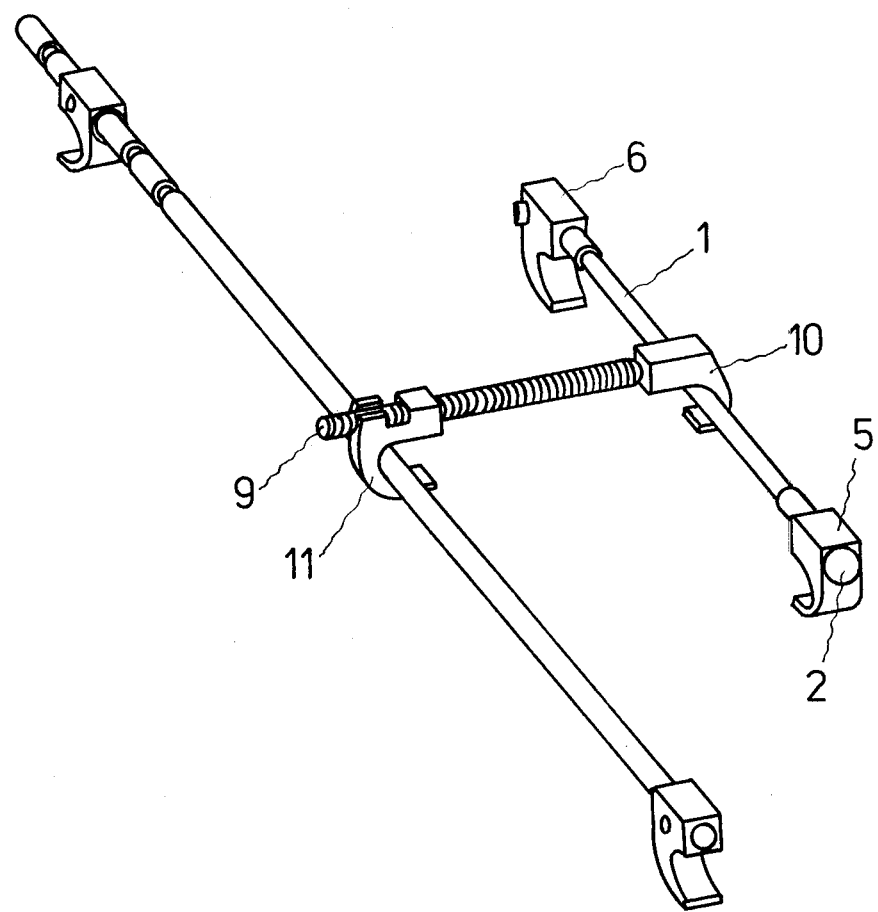
FIG. 7 shows a view of the device according to the invention as fixed in the patient's body.

The device comprises a profiled bar 1 constituting a longitudinal contractor, the said bar being provided at one end with a bearing surface 2 and at the other end—with tips 3 and 4, and fixed in holes of hooks 5 and 6 placed between appropriate vertebrae of the spine under treatment. Position of hook 5 is adjusted by means of bearing surface 2, whereas position of hook 6 provided with symmetrical recesses 7 and 8 made at the outer edge of its hole is adjusted by means of plastic deformation of tips 3 and 4 of bar 1. Bar 1 of a longitudinal contractor is connected with the known distraction spacer by means of a transverse contractor made in the form of threaded pin 9, one end of which is provided with a fixed catch 10 and the other end—with tilting catch 11. Tilting catch 11 is provided with a thread lock in the form of a threaded hole, one end of which has a bevelled internal surface 12, whereas the other end has a recess, protruding elements 13—after being bent—protecting the lock against inclination and dislocation.

What is claimed is:

1. In a device for treatment of spinal curvature comprising a distraction spacer adapted to be attached to the extreme vertebrae of the spinal curvature, a longitudinal contractor comprising a rod having hooks at its opposite ends, said hooks being adapted to be attached to the most displaced vertebra of the curvature, one of said hooks being fixed to said rod and the other of said hooks being slidable along said rod, and a transverse contractor comprising a threaded bar having a stationary hook at one end engageable with said rod and slidable hook at the other end engageable with said distraction spacer, the improvement wherein one end of said rod of said longitudinal contractor has two parallel end pieces which are displaceable outwardly to prevent outward longitudinal displacement of the slidable hook of said longitudinal contractor, and said slidable hook of said transverse contractor is provided with a tiltable grip for engaging said threaded bar, said grip having a partially threaded hole engageable with the threads of said bar, and on an axis intersecting the axis of said hole, an obliquely cut inner face and a cutout opposite said inner face defining spaced ears which are bendable into engagement with said bar to fix said slidable hook of said transverse contractor in position on said threaded bar.

* * * * *

UNITED STATES PATENT AND TRADEMARK OFFICE
CERTIFICATE OF CORRECTION

PATENT NO. : 4,257,409
DATED : March 24, 1981
INVENTOR(S) : Kazimierz BACAL and Lech WIERUSZ It is certified that error appears in the above—identified patent and that said Letters Patent is hereby corrected as shown below:

Title page; below "[76] Inventors:" and above "[21] Appl. No." please insert --[73] Assignee: Wyzsza Szkola Inzynierska im. J. Gagarina, of Zielona Gora, Poland--.

Signed and Sealed this

Seventh Day of July 1981

[SEAL]

Attest:

RENE D. TEGTMEYER

Attesting Officer

Acting Commissioner of Patents and Trademarks